United States Patent [19]

Enomoto

[11] Patent Number: 4,984,453

[45] Date of Patent: Jan. 15, 1991

[54] INDENTER FOR FRACTOEMISSION MEASUREMENT

[75] Inventor: Yuji Enomoto, Tsukuba, Japan

[73] Assignees: Agency of Industrial Science & Technology; Ministry of International Trade and Industry, both of Tokyo, Japan

[21] Appl. No.: 475,278

[22] Filed: Feb. 5, 1990

[30] Foreign Application Priority Data

Feb. 13, 1989 [JP] Japan .................................. 1-32930

[51] Int. Cl.⁵ .............................................. G01N 3/48
[52] U.S. Cl. .................................................... 73/81
[58] Field of Search ..................... 324/158 F, 158 P; 73/81, 82, 85

[56] References Cited

U.S. PATENT DOCUMENTS

| | | | |
|---|---|---|---|
| 1,571,310 | 2/1926 | Wilson | 73/85 |
| 4,406,373 | 9/1983 | Braden | 324/158 F |
| 4,544,888 | 10/1985 | Knaternik | 324/158 P |
| 4,551,675 | 11/1985 | Heys et al. | 324/158 F |
| 4,566,184 | 1/1986 | Higgins et al. | 324/158 P |
| 4,695,788 | 9/1987 | Marshall | 324/158 D |
| 4,829,238 | 5/1989 | Goulette et al. | 324/158 P |
| 4,855,673 | 8/1989 | Todokoro | 324/158 P |
| 4,893,077 | 1/1990 | Auchterlonie | 324/233 |

FOREIGN PATENT DOCUMENTS 232579 11/1968 U.S.S.R. .................................. 73/81

Primary Examiner—Robert Raevis
Attorney, Agent, or Firm—Oblon, Spivak, McClelland, Maier & Neustadt

[57] ABSTRACT

Indenter for fractoemission measurement which is comprised of a nonconductive holder and in which the tip that contacts the specimen surface is formed of a hard, conductive material. The entire surface, except for the tip that contacts the specimen, is covered with electromagnetic shielding.

8 Claims, 6 Drawing Sheets

INDENTER FOR FRACTOEMISSION MEASUREMENT

BACKGROUND OF THE INVENTION

1. Field of the Invention

This invention relates to an indenter for measurement of fractoemissions from specimens being subjected to indentation hardness testing, scratch testing and other such tests by a material tester.

2. Prior Art Statement

Hardness testers are used for measuring material properties such as hardness and toughness. This is done by loading a specimen of the material with an indenter formed of a hard material such as diamond, and measuring the size of the indents and cracks thus produced in the specimen. Scratch hardness is determined by measuring the width of scratches produced on the surface of the specimen by an indenter. Thus, tests such as these are used to examine the mechanical properties of materials.

It is known that deformation and fracturing of solids, especially inorganic materials, induces the emission of charged particles such as electrons and ions. It is also known that the mechano-electrical properties of the materials can be ascertained by examining these emissions. Most of the detectors used for detecting such emission are electrode-based current collectors such as channeltrons, Geiger-Muller tubes and the like, which have to be operated in a vacuum or in a special gaseous environment. Hardness testing under atmospheric conditions has therefore been limited to measuring the above mechanical properties by examining deformation and cracking produced in the surface of the material being tested.

This has given rise to a strong demand for the development of a technique that would enable both charged particle emissions and mechanical properties to be measured at the same time.

OBJECTS AND SUMMARY OF THE INVENTION

An object of this invention is therefore to provide an indenter for fractoemission measurement that enables the simultaneous measurement of mechanical properties and charged particle emissions, under atmospheric conditions.

For attaining the aforesaid object the present invention provides an indenter for fractoemission measurement comprising a holder portion constituted of a nonconductive material and an indenter tip formed of a hard, electroconductive material, the indenter thus constituted being covered with electromagnetic shielding except for the said conductive tip, which is the part that actually contacts the specimen (also referred to as the test piece).

In an indentation hardness tester, the indenter thus constituted is used to load the surface of a specimen of the material being tested, under atmospheric conditions, as in the case of a conventional test, and the hardness and toughness of the material is determined from the size of the resulting indentation and the length of the cracks around the contact zone. In the case of a scratch hardness tester, scratch hardness is determined by measuring the width of scratches made by the indenter on the surface of the test piece.

With respect to the measurement procedure, fractoemission from the test piece occurs when the indenter is loaded on the test piece and when the indenter is unloaded, and also when the test piece is being scratched.

As the indenter of this invention is conductive, applying a bias voltage enables charged particles to be collected efficiently by the indenter in direct contact with the material being tested, thereby enabling the mechano-electrical properties of the material to be ascertained.

As the whole of the conductive portion of the indenter is covered with shielding to protect the indenter against external electrostatic noise, the indenter collects only charged particle from the test piece, providing accurate emission measurement.

The above and other features and objects of the invention will become apparent with the following detailed description made with reference to the attached drawings.

DETAILED DESCRIPTION OF THE PREFERRED EMBODIMENTS

Figure 1:
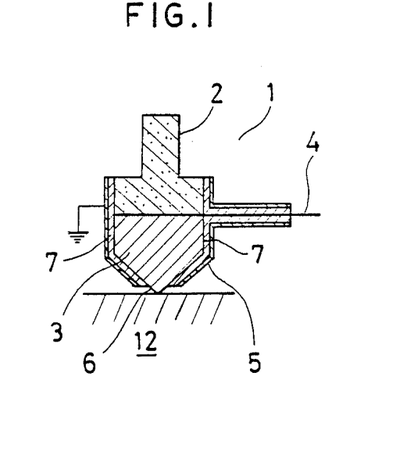
FIG. 1 is a cross-sectional view of a first embodiment of the indenter according to the invention.

FIG. 1 shows a first embodiment of the invention in which the indenter is used in a Rockwell indentation hardness tester. The indenter 1 has a holder portion 2 which is inserted into the tester, and a front end portion 3. The holder portion 2 is formed of zirconia or other such nonconductive material. The front end portion 3 is formed of a hard, conductive material such as $B_4C$ or a sintered composite ceramic of a mixture of $ZrB_2,B_4C$ and SiC, and is securely attached to the holder portion 2 by adhesive cement, for example. A tip radius of 200 $\mu$m and an apex angle of 120° was used for the conical tip 6 of the end portion 3, in accordance with standards covering Rockwell hardness testers. One end of a lead wire 4 is electrically connected to a computing circuit, which is described later.

The end portion 3 of the indenter 1 and the lead wire 4 are covered with grounded electromagnetic shielding 5 which has an electrically insulating relation to the end portion 3 and lead wire 4.

Figure 2:
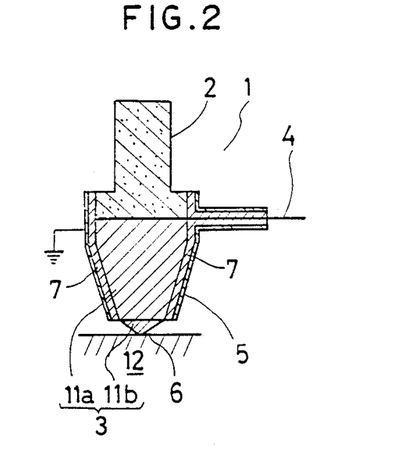
FIG. 2 is a cross-sectional view of a second embodiment of the indenter.

FIG. 2 shows an indenter according to a second embodiment in which the end portion 3 is comprised of a base portion 11a and a tip portion 11b. The base 11 is formed of stainless steel and the tip portion 11b is formed of conductive diamond the surface of which has been subjected to N or Ar ion implantation, or of boron-doped conductive type IIb diamond. In this embodiment, a layer of TiC is inserted between the stainless steel base portion 11a and the tip portion 11b, which were then diffusion-bonded. As in the first embodiment, except for the conical tip 6, the end portion 3 and the lead wire 4 are covered completely by shielding 5.

Covering of the end portion 3 (except for the conical tip 6) and the lead wire 4 with the electromagnetic shielding 5 is effected, for example, by using an insulating tape made of Teflon etc. as the shielding 5 and winding the tape on the end portion 3 and lead wire 4 or by coating the end portion 3 and lead wire 4 with an insulating substance 7 made of an insulating ceramic material etc., using as the shielding 5 aluminium or copper foil with adhesive attached to the rear surface thereof and applying the foil to the insulating substance 7.

The indenter 1 thus constituted is fitted in an electrically nonconductive state on the hardness tester, and is then used to load the surface of the specimen 12 to enable the hardness of the specimen 12 to be determined on the basis of the indentation thus formed.

The indenter of this invention allows charged particle emissions from the specimen 12 to be measured at the same time as the hardness testing. For this, with reference to FIG. 3, the lead wire 4 is connected to a charge detector 13 which is connected to an integrating unit 14 which is connected to a computing circuit 15. The computing circuit 15 issues a signal to energize a trigger unit 17 and causes the indenter 1 to be loaded by a prescribed amount 16, causing indentation of the surface of the specimen 12 by the tip of the indenter 1. During this time, a bias voltage of prescribed polarity is applied to the indenter 1. Cracking of the specimen 12 caused by the loading of the indenter 1 is accompanied by emissions from the specimen 12 of charged particles such as electrons and negative ions. Applying a positive bias to the indenter 1 will cause the indenter 1 to collect electron and negative ion emissions from the specimen 12, while a negative bias will cause positive ions to be collected. The application of a bias voltage to the indenter 1 during this procedure increases the susceptibility of the indenter 1 to external electrostatic noise. As a shield against such electrostatic noise therefore, electromagnetic shielding 5 is used as a shield against such electrostatic noise so as to cover the portion of the indenter 1 that does not contact the specimen 12. In other words, only the tip 6 of the indenter 1 is left uncovered.

Figure 3:
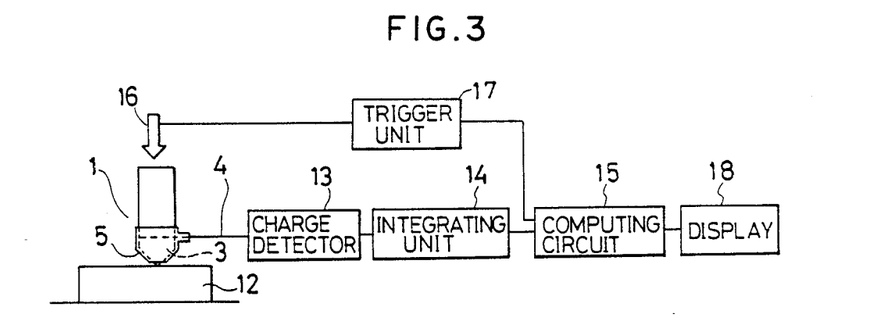
FIG. 3 is a schematic diagram of the apparatus for detecting and processing charged particles collected by the indenter.

Thus, the charged particles emitted by the specimen 12 flow to the end portion 3 and are transmitted via the lead wire 4 to the charge detector 13 where they are converted to electrical signals, amplified and fed to the sampling integrating unit 14, where signals input at prescribed intervals are integrated. The computing circuit 15 then computes time-based changes in the detected intensity of collected charged particles and displays the results on a CRT or other such display unit 18.

Also detected are charged particles emitted during changes in the load on the specimen 12 and when the indenter 1 is unloaded.

As described above, the tip of the indenter of the invention is formed of a conductive material and is shielded from outside electrostatic noise by electromagnetic shielding, enabling it to efficiently collect, either directly or indirectly, only charged particles emitted by the test piece, even under atmospheric conditions.

Figure 4:
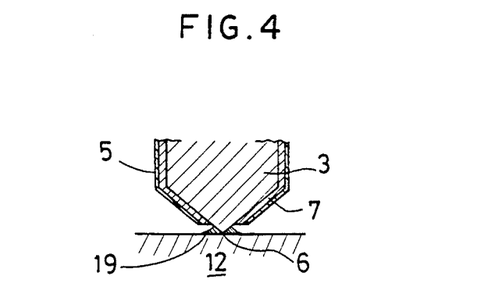
FIG. 4 is an explanatory diagram showing the indenter of the invention being used for measurements on a liquid.

The invention will now be described with reference to hardness testing in liquid. As shown in FIG. 4, a drop of liquid 19 is first placed on the specimen 12 at a prescribed location and a prescribed load is then applied to the indenter 1 so that the tip 6 comes into contact with the surface and makes an indentation at that position. The indentation thus formed reveals the mechanical properties of the material subjected to the effects of the liquid, and at the same time the electrical properties are ascertained on the basis of time-based changes in the intensity of charged particles collected by the indenter.

The indenter of this invention can also be used as a scratch hardness tester indenter, thereby providing reliable collection of charged particle emissions occurring during the course of scratch testing.

The embodiments will now be described in further detail. A Rockwell type indenter (apex angle: 120°, tip radius: 200 $\mu$m) having a holder of partially stabilized zirconia (PSZ) and an end portion of boron carbide ($B_4C$) was used. The portion of the indenter except for the tip thereof was coated with a Teflon tape, and aluminium foil having adhesive attached to the rear surface thereof was applied as an electromagnetic shielding to the Teflon tape. This indenter was mounted on a hardness tester (manufactured by Akashi Co., a Japanese corporation) and subjected to procedures comprising the steps of biasing the indenter at +15 V, bringing the tip of the indenter into contact with a single crystal of lithium fluoride (LiF) in the atmosphere for 1.2 seconds, then loading the indenter so as to have a load of 20 kgf, maintaining the loaded state for 1.2 seconds, and unloading the indenter.

Figure 5:
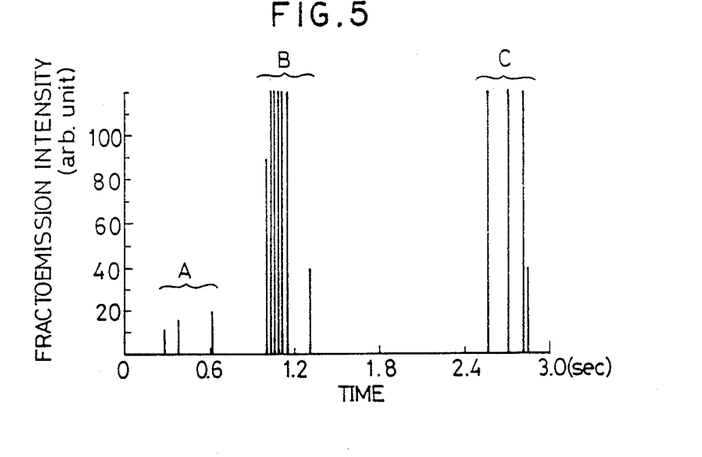
FIG. 5 is a graph showing time-based changes in the detected intensity of charged particles collected during an indentation test with the indenter of this invention.
Figure 6A:
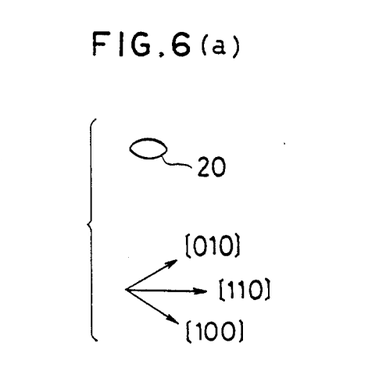
FIG. 6(a) is a drawing of an indentation produced in a test piece by the indenter of the invention.
Figure 6B:
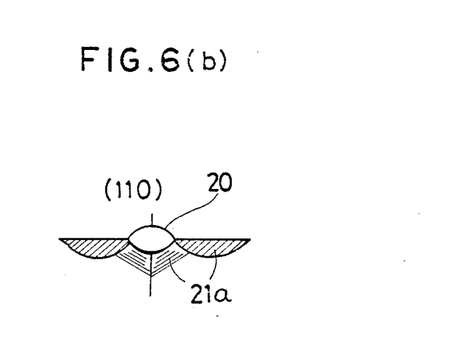
FIG. 6(b) is a drawing showing the crack formation produced when the indenter loading is increased.
Figure 6C:
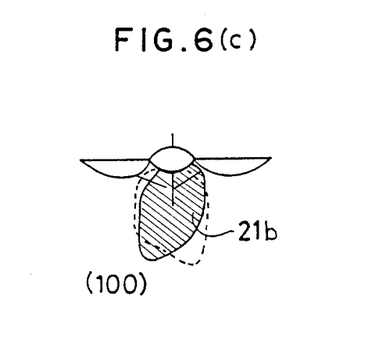
FIG. 6(c) is a drawing showing cleavage cracks produced at maximum loading.
Figure 6D:
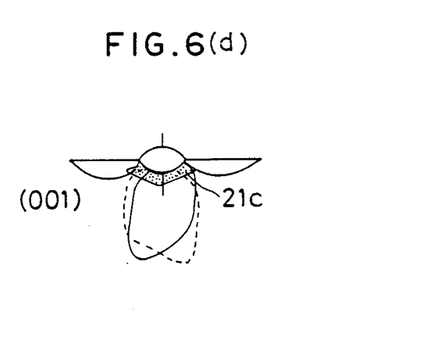
FIG. 6(d) is a drawing showing cleavage cracks produced when the indenter is unloaded.

FIG. 5 is a graph of the detected intensity of electron emissions collected from the LiF specimen, plotted against time, and FIG. 6 shows the evolution of the deformation and cleavage cracking in the specimen.

Indentation is initiated when the indenter tip touches the LiF surface. Indentation cracking starts with the small surface indentation 20 shown in FIG. 6(a), which is followed by the (110) radial cracks 21a shown in FIG. 6(b). At this point the intensity of collected electron emissions (indicated by A in FIG. 5) is very low. When the full load of 20 kgf is reached at the end of the 1.2 second loading half cycle, median cracks 21b appear on the LiF (100) surface. As shown by B in FIG. 5, at this time electron emission intensity reaches a peak.

No electrons were collected during the period of constant full loading at 20 kgf, indicating no further cracking took place during this period. The unloading after 2.4 seconds resulted in the collection of electrons as shown at C in FIG. 5, with the formation of (001) lateral cracks 21c shown in FIG. 6(d).

As described above, the indenter according to this invention enables charged particle emissions accompanying the formation of cleavage cracking in a specimen to be readily detected.

Next, an indenter with the same configuration as the one in the embodiment described above was used to apply an indentation load of 10 kgf to the (111) surface of a calcium fluoride ($CaF_2$) specimen. The indenter was given a +15 V d.c. or −15 V d.c. bias for the collection of either negative charge particle emissions (electrons and negative ions) or positive ion emissions accompanying indentation cracking of specimens.

Figure 7A:
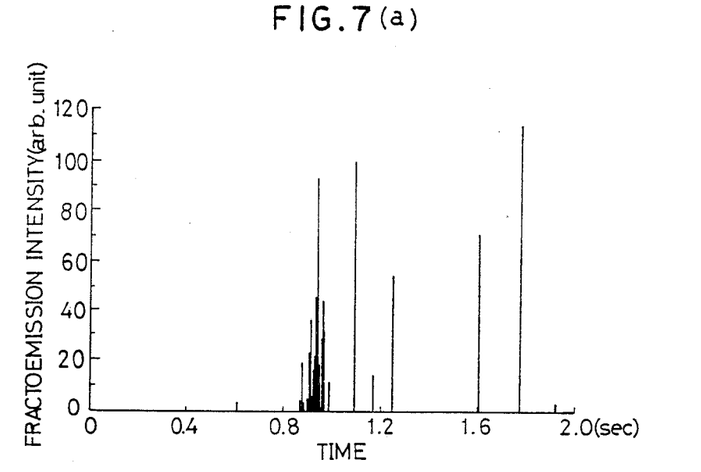
FIG. 7(a) is a graph showing time-based changes in the detected intensity of negative charges collected during an indentation test on calcium fluoride with the indenter of this invention.
Figure 7B:
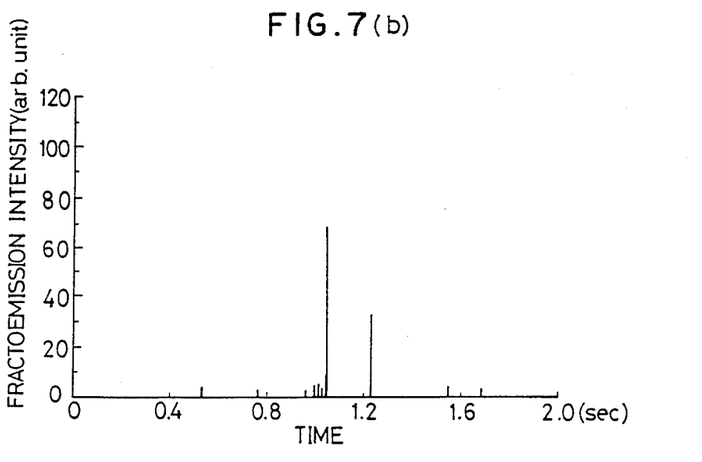
FIG. 7(b) is a graph showing time-based changes in the detected intensity of positive ions collected during an indentation test on calcium fluoride with the indenter of this invention.

FIG. 7(a) shows negative charge particles collected using a positive d.c. bias and FIG. 7(b) shows positive ions collected using a negative d.c. bias.

On an integrated basis, the amount of negative fractoemissions was about six times the amount of positive fractoemissions, partly owing to the high mobility of electrons in the negative emissions.

Figure 8:
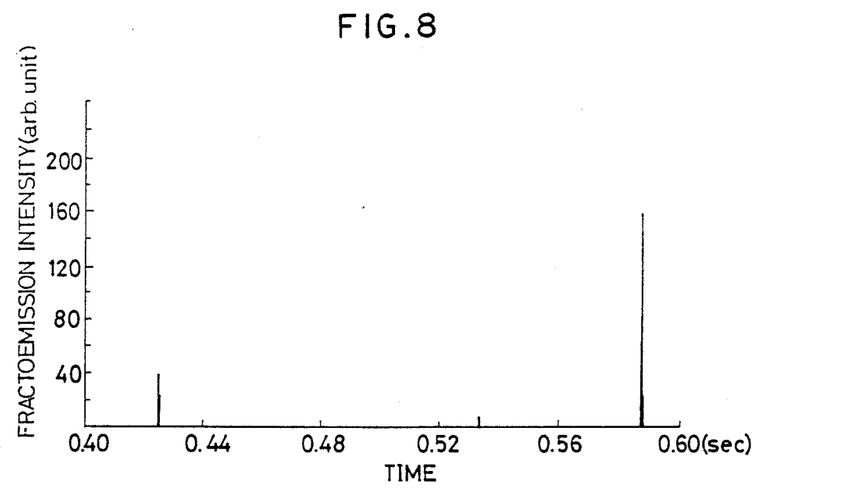
FIG. 8 is a graph showing time-based changes in the detected intensity of charged particles collected during an indentation test on MgO with the indenter of this invention.

A Rockwell specification indenter made of boron carbide with the same configuration as the one described above, supported by a holder of zirconia, and with a +15 V d.c. bias, was used to apply an indentation load of 20 kgf to the surface of a magnesium oxide (MgO) specimen. FIG. 8 is a graph of the detected intensity of electron emissions collected from the specimen in air, plotted against time. The current intensity shows a sudden rise when the indenter starts to penetrate the surface (at about 430 ms) and when the indenter is unloaded (at about 590 ms), indicating that there was an emission of negatively charged particles, that is, electrons.

Figure 9A:
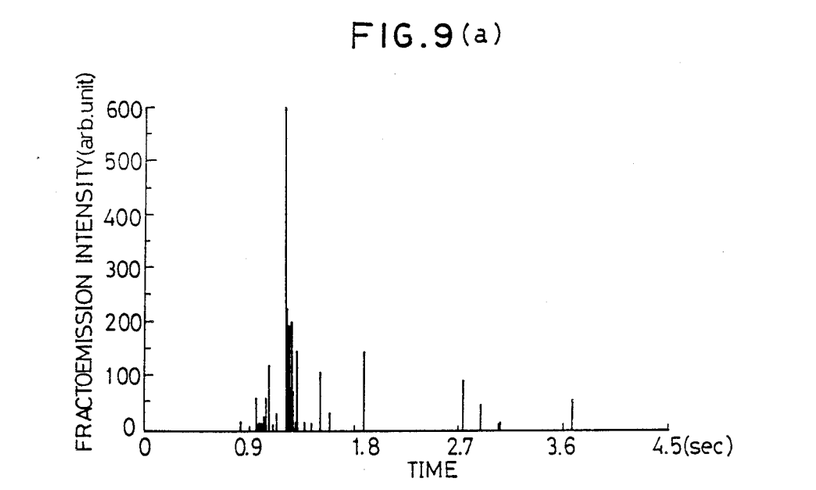
FIG. 9(a) is a graph showing time-based changes in the detected intensity of charged particles collected during an indentation test on mica with the indenter of this invention.

Another indentation test was conducted, under the same conditions, on a mica specimen. As shown by the graph of FIG. 9(a), sharp rises in intensity occurred when the indenter started to penetrate the surface (at about 1.0 sec), with the formation of radial cracks (at about 1.2 sec), with the formation of median cracks (1.8–2.7 sec) and when the indenter was unloaded (at about 3.6 sec), indicating that emissions of electrons took place.

Figure 9B:
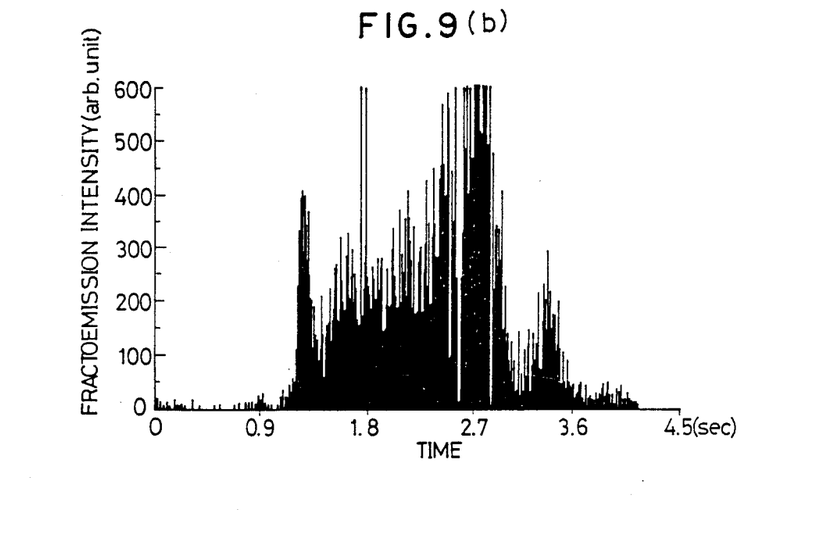
FIG. 9(b) is a graph showing time-based changes in the detected intensity of charged particles collected during an indentation test carried out under the same conditions as the test relating to FIG. 9(a), using an indenter that is not provided with electromagnetic shielding.

For comparison, a mica indentation test was conducted under the same set of conditions except that the indenter was not provided with electromagnetic shielding. The results, as shown in FIG. 9(b), show that the indenter picked up a considerable amount of electrostatic noise, which made it difficult to distinguish signals produced by fractoemission from the mica.

Figure 10:
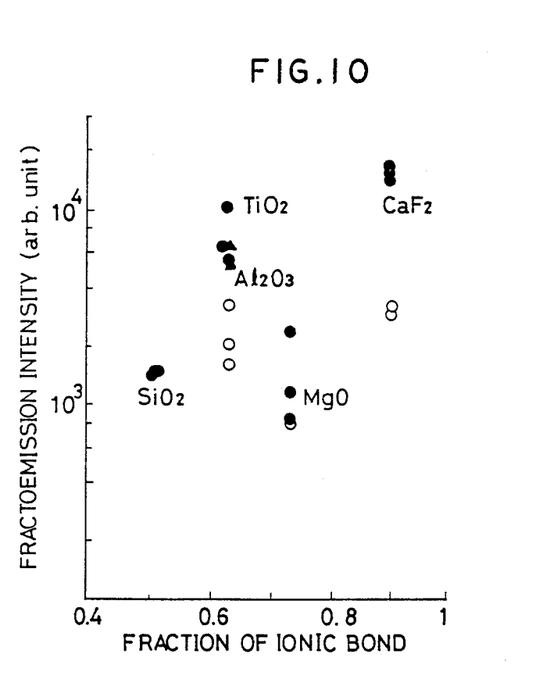
FIG. 10 shows the total amount of charged particles collected during indentation testing in which the test pieces were superhard single crystals.

FIG. 10 shows the relationship between crystal ion bonding and fractoemission during indentation fracturing of specimens of $SiO_2$, $TiO_2$, $Al_2O_3$, MgO and $CaF_2$, using an indenter of the same above-described configuration and a loading of 20 kgf. It can be seen that emission intensity was greater in the case of $CaF_2$, which has a high fraction of ionic bond, and $TiO_2$, which has a high dielectric constant. In the graph, a filled circle indicates electron collection with a positively biased indenter and a blank circle indicates collection of positive ions with a negatively biased indenter.

Figure 11:
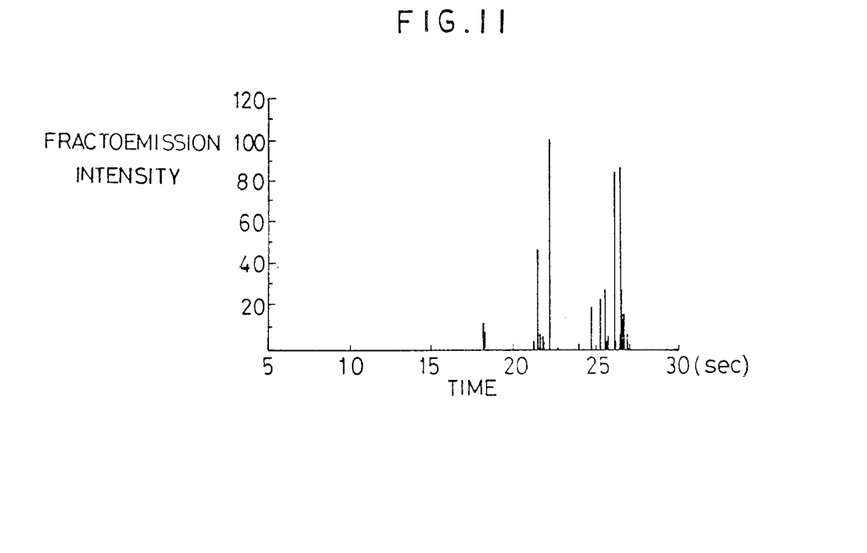
FIG. 11 is a graph showing time-based changes in the detected intensity of charged particles collected during a scratch test using the indenter of this invention.
Figure 12:
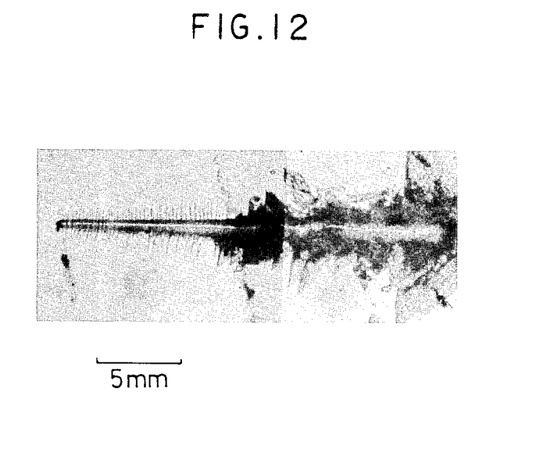
FIG. 12 is an optical micrograph of the scratching produced by the scratch test of FIG. 11.

Each of the above embodiments has been described with reference to indentation testing. The indenter of this invention can also be applied to scratch testing, an embodiment of which will now be described. An indenter having the same construction as the indenter used for indentation testing and conforming to Rockwell specifications, was biased and used to subject the surface of a LiF (001) surface to scratching in the [110] direction at load that was increased continuously from 0 to 2.5 kgf while measuring negative charge fractoemissions. FIG. 11 shows the results, and FIG. 12 is an optical micrograph of the scratch fracturing thus produced.

Extensive fracturing of the specimen when the load was increased was accompanied by intense fractoemission. The results plotted on the graph and the fracturing as shown in the photograph are substantially in agreement.

Thus, as has been described in the foregoing, in place of the diamond used as the nonconductive material generally used in conventional indenters, the indenter according to the present invention is electroconductive, being constituted of a conductive material such as boron carbide or type IIb diamond or of diamond the surface of which is made conductive by ion implantation. The indenter thus formed is electrically insulated from the tester, so that it forms an electrode whereby charged particles can be collected and measured. As the indenter/electrode can thus directly contact the surface of the specimen which is the source of the charged particle emissions, loss of charged particles in air can be minimized. This provides a more efficient collection of charged particles than other methods in which the electrode is separated from the surface of the specimen.

What is claimed is:

1. An indenter for measuring the fractoemission and hardness of a test piece, comprising:
   a nonconductive holder portion;
   a front end portion constituted of a conductive material supported at the lower end of said holder portion and having a tip that contacts said test piece for producing indents and scratches in said test piece;
   electromagnetic shielding which covers the exterior of the front end portion except for said tip; and
   a lead wire, one end of which is electrically connected to said front end portion for external transmission of charged particles collected by said tip.

2. An indenter according to claim 1, wherein said front end portion is formed of $B_4Cr$ or a sintered composite ceramic of a mixture of $ZiB_2$, $B_4C$ and $SiC$.

3. An indenter for fractoemission measurement according to claim 1 wherein the front end portion has a copper base and the tip is conductive diamond.

4. An indenter for fractoemission measurement according to claim 3 wherein the conductive diamond is diamond subjected to surface implantation of N ions.

5. An indenter for fractoemission measurement according to claim 3 wherein the conductive diamond is diamond subjected to surface implantation of Ar ions.

6. An indenter for fractoemission measurement according to claim 3 wherein the conductive diamond is boron-doped type IIb diamond.

7. An indenter for fractoemission measurement according to claim 1 in which the electromagnetic shielding is copper or aluminium foil.

8. An indenter for fractoemission measurement according to claim 1 wherein the front end portion of said indenter except for the tip thereof is coated with an insulating substance and said electromagnetic shielding covers said insulating substance.

* * * * *